United States Patent

Rose

[11] Patent Number: 5,256,978
[45] Date of Patent: Oct. 26, 1993

[54] MICROWAVE MOISTURE CONTENT ANALYZER

[76] Inventor: Mitchell Rose, 3718 Silsby Rd., University Heights, Ohio 44118

[21] Appl. No.: 874,084

[22] Filed: Apr. 27, 1992

[51] Int. Cl.⁵ .......................................... G01R 27/04
[52] U.S. Cl. ..................................... 324/601; 324/643
[58] Field of Search ............... 324/332, 333, 632, 634, 324/640, 643, 601

[56] References Cited

U.S. PATENT DOCUMENTS

| | | |
|---|---|---|
| 3,644,826 | 2/1972 | Cormetet, Jr. |
| 4,013,950 | 3/1977 | Falls ..................................... 324/332 |
| 4,156,843 | 5/1979 | Strandberg, Jr. et al. |
| 4,361,801 | 11/1982 | Meyer et al. |
| 4,364,008 | 12/1982 | Jacques |
| 4,399,403 | 8/1983 | Stranberg ............................ 324/640 |
| 4,485,284 | 11/1984 | Pakulis |
| 4,727,311 | 2/1988 | Walker |
| 5,001,433 | 3/1991 | Osaki .................................. 324/632 |

OTHER PUBLICATIONS

Rzepecka, et al., "Monitoring of Concrete Curing Process by Microwave Terminal Measurements", IEEE Trans. on Indust. Elect. and Control Instru., vol. 19, No. 4, Nov., 1972.

*Primary Examiner*—Kenneth A. Wieder
*Assistant Examiner*—Jose M. Solis

[57] ABSTRACT

A device and method for measuring the moisture content of a sample using microwaves is provided. The device includes a power supply for outputting an electrical current, a microwave oscillator electrically connected to the power supply for outputting a microwave signal, and a waveguide placed between the microwave oscillator and the sample. The waveguide has a predetermined length and is constructed from copper. A microwave detector outputs a voltage signal which is related to the intensity of the microwave energy reflected by moisture in the sample. A voltmeter displays a reading of the voltage signal output by the microwave detector. The length of the waveguide is selected to maximize the voltage reading of the voltmeter for a given sample. An enclosure houses the power supply, the microwave oscillator, the waveguide and the microwave detector, and is provided with an opening at which the waveguide is mounted. A sheet of microwave transmissive material covers the opening.

10 Claims, 1 Drawing Sheet

MICROWAVE MOISTURE CONTENT ANALYZER

This invention was made with U.S. Government support and the Government has certain rights in the invention.

FIELD OF THE INVENTION

The present invention relates generally to microwave devices and more particularly to a device for measuring the moisture content of a sample using microwaves which are reflected by moisture in the sample.

BACKGROUND OF THE INVENTION

Aquametry is a method of determining the moisture content of solids and liquids and is practiced in numerous industries. For example, the determination of moisture content is important in grain to determine propensity for spoilage, in soil to determine irrigation requirements, in sand to determine proper water proportioning in batching concrete, in paper manufacturing to verify requisite dryness, and in food processing to verify appropriate cooking times. Common venues for moisture determination include laboratories for research and quality control, inside storage bins, and within processing equipment to measure moisture during various processes.

The most common methods of moisture determination include measuring weight loss upon heating, measuring humidity within a cavity containing the sample, and various titration methods. None of these methods, however, are nondestructive, nonintrusive and instantaneous.

Microwave based aquametry methods are categorized as either transmissive or reflective, and are based on the high dielectric constant of water which causes moisture to be both highly absorptive and reflective in the microwave and infrared regions. Commercially available infrared reflectance devices sense only surface moisture. Known commercially available microwave transmission methods are susceptible to interferences due to extraneous reflections and embedded metal in the sample being analyzed, require access to opposite sides of the sample, and are limited to measuring low bulk moisture because of the high absorptivity of water.

U.S. Pat. No. 4,364,008 to Jacques discloses a moisture content analyzer which utilizes the capacitive method of measuring moisture content. The capacitive method entails measuring the increase in electrical capacitance caused by placing the sample within the electric field of a capacitor. In the Jacques patent, an electromagnetic wave created by an oscillating electric field distributes itself so that a standing wave occurs in a resonant cavity. Moisture in the sample interacts with the electromagnetic wave to shift the frequency of the standing wave. The magnitude of the shift is determinative of the amount of moisture in the sample. Being capacitive in nature, the disclosed method requires a larger sample than is necessary for other methods of moisture determination.

U.S. Pat. No. 4,156,843 to Strandberg, Jr. et al. discloses a microwave reflectance based moisture indicator for thin webbed material. The Strandberg device irradiates the sample with an X-band Gunn oscillator and measures the reflected energy with a diode detector. Both the source and the receiver are fitted with horns which are angularly mounted with respect to each other on one side of the moving web.

Rzepecka, et al., "Monitoring of Concrete Curing Process by Microwave Terminal Measurements", *IEEE Transactions on Industrial Electronics and Control Instrumentation*, Vol. 19, No. 4, November 1972, discloses a method of monitoring concrete curing processes using microwaves. The device described in the article utilizes a single horn serving as both the source and the receiver through use of a directional coupler. The device is used to study dielectric changes in hydrating concrete, but not to quantitatively measure moisture.

Microwave aquametry techniques, particularly transmissive techniques, are adversely affected by numerous reflections from the sample surfaces, the microwave components, and the environment. These multiple reflections give rise to a wave propagation pattern that is extremely complex, varies greatly with even small variations in sample size and component positioning, and is impractical to predict.

Accordingly, there is a need for a simple and inexpensive microwave moisture analyzer which operates in the reflective mode and which requires no receiver or transmitter horns or antennae. The present invention addresses this need by providing a microwave moisture analyzer which operates in a nondestructive and noninvasive manner and which provides an instantaneous indication of the moisture content of a sample being analyzed.

SUMMARY OF THE INVENTION

A device that measures the moisture content of non-electrically conductive homogeneous solid and liquid samples is provided. The device indicates the relative moisture content by measuring the extent to which the samples reflect microwaves. The method by which the measuring proceeds is both nonintrusive and nondestructive. The device comprises an enclosure which houses a regulated DC power supply, a microwave transceiver module, flange fittings secured to the module and a waveguide inserted within the flange fittings.

The microwave transceiver module is a microwave Doppler-effect transceiver commonly used for police radar, motion detectors, and automatic door openers. The transceiver module includes a microwave oscillator for transmitting a microwave signal toward the sample and a detector for sensing microwaves reflected back from the moisture in the sample. The waveguide is placed between the transceiver and the sample, and its length is selected so that the transmitted and reflected waves are in phase at the detector. The output of the detector is a voltage which is related to the amplitude of the vector sum of the transmitted and reflected waves at the detector. The amplitude of the reflected signal is related to the moisture content of the sample. The voltage output of the detector is connected to a voltmeter which provides an indication of the relative moisture content of the sample being analyzed. The greater the moisture content in the sample, the higher the amplitude of the reflected microwave signal.

The sensitivity of the device is maximized if the transmitted and reflected signals are in phase at the detector. This is achieved by adjusting the length of the waveguide to yield a maximum voltmeter reading for a given sample.

DETAILED DESCRIPTION OF THE PREFERRED EMBODIMENT

Figure 1:
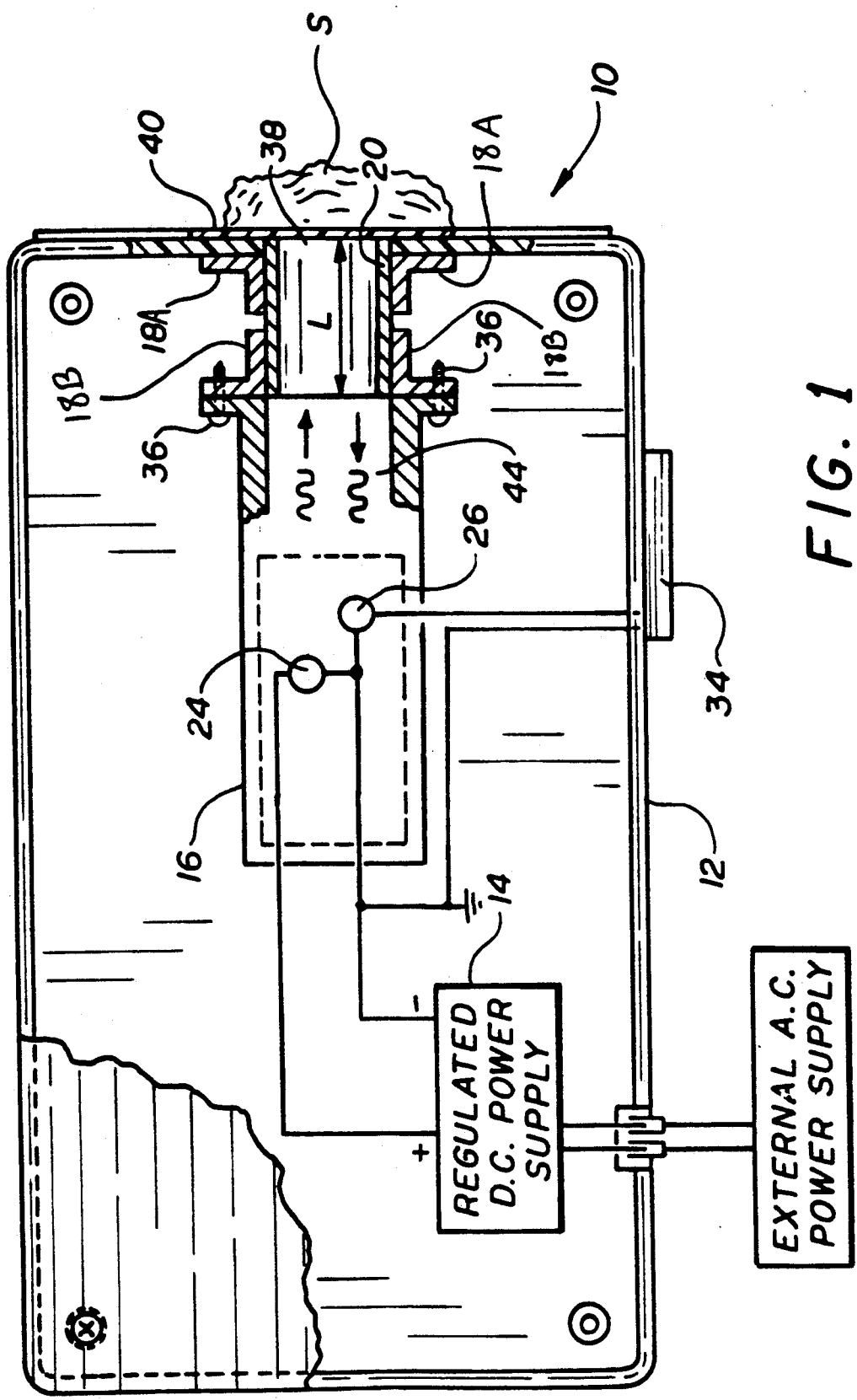
FIG. 1 is a partially cutaway schematic view of a microwave device for measuring moisture content, constructed according to the principles of the present invention.

FIG. 1 is a schematic diagram showing a microwave moisture content analyzer device 10 constructed according to the principles of the present invention. The device 10 indicates the moisture content of a homogeneous sample S placed in close proximity to the device. The device 10 comprises an enclosure 12 which houses a regulated DC power supply 14, a microwave transceiver module 16, flange fittings 18A and 18B secured to the module 16 and a waveguide 20 inserted within the flange fitting 18.

The enclosure may be constructed of any suitable material, such as plastic, and provides protection from the environment for the internal components of the device 10. The output of the supply 14 depends on the requirements of the microwave transceiver module 16, and is typically between six and twenty-four volts DC.

The microwave transceiver module 16 is, in the preferred embodiment, a microwave Doppler-effect transceiver such as the commercially available Model No. GOS2580 from Alpha Industries, Inc. of Woburn Mass. Such a transceiver is commonly used for police radar, motion detectors, and automatic door openers. The preferred transceiver module 16 includes a microwave oscillator 24 and a detector 26 for sensing microwaves reflected back from the moisture in the sample S. The microwave oscillator is a gallium-arsenide Gunn diode which is mounted in a waveguide cavity. The Gunn diode operates in the X band. The detector 26 is a Schottky barrier mixer diode.

The output of the mixer diode 26 is a voltage which is related to the amplitude of the sum of the transmitted and reflected waves at the detector 26. The amplitude of the reflected signal is related to the moisture content of the sample. The voltage output of the mixer diode 26 is connected to a voltmeter 34. The voltmeter 34 thus provides an indication of the relative moisture content of the sample S being analyzed.

The preferred microwave transceiver module 16 mates with the flange fittings 18A and 18B. Fasteners such as screws 36 are used to fasten the flange fitting 18B to the module 16. The flange fittings 18A and 18B provide a 0.5"×1.0" opening wherein the waveguide 20 may be installed. The waveguide 20 provides the means to transmit the microwave signal output by the microwave oscillator 24 toward the sample S to be tested with no significant loss in signal strength.

The waveguide 20 is typically a 0.5"×1.0" copper channel of a predetermined length L. In addition to providing the means to transmit microwaves toward the sample, the waveguide also provides the means by which the portion of the signal which is reflected by moisture in the sample is guided back toward the microwave detector 26.

The enclosure 12 is provided with an opening 38 which permits the microwaves output by the microwave oscillator and transmitted by the waveguide to penetrate the sample S. A thin sheet 40 of microwave transmissive material, such as plastic, covers the opening 38 to assure that the sample does not protrude into the waveguide 20. In the preferred embodiment, the thickness of the sheet 40 is about one millimeter. The flange fittings 18A and 18B hold the waveguide 20 in place between the opening 38 and the transceiver 16. Other means, of course, are contemplated in place of the flange fittings 18A and 18B for this purpose.

In operation of the device, the sample S is placed directly upon the microwave transmissive sheet 40. To facilitate the procedure, the device 10 is positioned so that the sheet 40 is on top of the device, thereby forming a platform for the sample. If the sample is difficult to place directly on the sheet 40, such as a powder or liquid, it may be contained in a thin bottomed receptacle which is placed atop the plastic sheet 40.

The microwave oscillator 24 generates a microwave signal which passes through a cavity 44 in the transceiver module 16, through the copper waveguide 20 and the microwave transmissive sheet 40, and penetrates the sample S. The depth at which the microwaves penetrate the sample before being reflected (i.e., the depth of sensitivity to moisture) depends on the wavelength used and the type of sample being analyzed. Microwaves in the preferred embodiment will penetrate water less than one-tenth inch, but will penetrate a fairly dry sand sample more than one inch. The thickness of the sample required must be at least the depth to which the microwaves will penetrate the sample S.

A portion of the output of the microwave oscillator 24 is leaked to the mixer diode 26. Moisture in the sample will reflect microwaves back through the transmissive sheet 40, the waveguide 20 and the cavity 44 toward the mixer diode 26. The more moisture in the sample, the higher the amplitude of the reflected microwave signal. The mixer diode 26 outputs a voltage related to the amplitude of the sum of the transmitted and reflected waves. The voltmeter 34 displays this voltage. Accordingly, the voltmeter reading is related to the amount of moisture in the sample.

A user of the device 10 constructs a calibration plot of the voltmeter readings versus the moisture content of reference samples. The calibration plot is used to convert the voltmeter readings to moisture content for subsequent unknown samples. The height and shape of the calibration curve varies markedly with the length of the waveguide 20.

A portion of the microwave signal output by the oscillator 24 is leaked to the detector 26. If the waveguide 20 is of arbitrary length, the wave reflected from the sample and the wave leaked by the oscillator reach the detector phase shifted with respect to each other by an arbitrary phase angle. In this case, the slope of the calibration curve can be positive throughout its length, negative throughout its length, or negative at lower moisture levels and positive at higher moisture levels. The particular slope of the calibration curve will depend on the phase angle and the intensity of the leaked wave. A calibration plot having both a negative and positive slope yields ambiguous results. Furthermore, whether positive or negative, the magnitude of steepness of the calibration curve, which indicates sensitivity of the device to moisture, is arbitrary.

Alternatively, if the waveguide 20 is of a specific length which causes the leaked and reflected waves to reach the detector exactly in phase with respect to each other, the performance of the device is optimized. The slope of the calibration curve will be positive throughout its length, and its steepness will be maximized, indicating optimal sensitivity to moisture.

To determine the waveguide length which optimizes performance as described above, a sample having any moisture content is positioned as shown in FIG. 1, and waveguides of various lengths are inserted as the waveguide 20. The waveguide length that renders the highest voltmeter reading is the length that optimizes the performance of the device in terms of shape and steepness of the calibration curve.

Accordingly, the preferred embodiment of a system for measuring the moisture content of a sample using microwave reflection has been described. With the foregoing description in mind, however, it is understood that this description is made only by way of example, that the invention is not limited to the particular embodiments described herein, and that various rearrangements, modifications, and substitutions may be implemented without departing from the true spirit of the invention as hereinafter claimed.

What is claimed is:

1. A device for measuring the moisture content of a sample, comprising:
   a microwave transceiver comprising a microwave oscillator for outputting a microwave signal toward the sample and a microwave detector for outputting a voltage signal which is related to the intensity of the microwave energy reflected from said sample, both said oscillator and said detector housed in a single cavity;
   a microwave transmitting waveguide with a calibrated length having one end set against said cavity;
   said waveguide calibrated length being determined by first placing a calibrating sample in close proximity to the other end of said waveguide, then measuring the voltage signal while incrementally reducing said waveguide length until said voltage signal is maximized.

2. The device of claim 1, wherein said microwave oscillator and said microwave detector are provided by a single Doppler-effect microwave transceiver unit.

3. A method of calibrating a device for measuring the moisture content of a sample, comprising the steps of:
   providing a microwave transceiver comprising a microwave oscillator for outputting a microwave signal toward the sample and a microwave detector for outputting a voltage signal which is related to the intensity of the microwave energy reflected from said sample, both said oscillator and said detector housed in a single cavity;
   providing a microwave transmitting waveguide having one end set against said cavity;
   placing a calibration sample in close proximity to the other end of said waveguide; and
   measuring said voltage signal while incrementally reducing said waveguide length until said voltage signal is maximized.

4. The method of claim 3, wherein said waveguide is constructed from copper.

5. The device of claim 2, further comprising an enclosure for housing a power supply, said microwave oscillator, said waveguide and said microwave detector, said enclosure having an opening at which said waveguide is mounted.

6. The device of claim 5, further comprising a sheet of microwave transmissive material covering said opening.

7. The device of claim 6, wherein said sheet of microwave transmissive material has a thickness of between 0.5 and 1.5 mm.

8. The device of claim 7, wherein said microwave oscillator operates at between 1 and 24 gigahertz.

9. The method of claim 4, further comprising the steps of (i) providing an enclosure for housing said transmitter, said detector and said waveguide, and (ii) placing a sheet of microwave transmissive material between the sample and said enclosure.

10. The device of claim 2, further comprising a one piece enclosure for housing said power supply, said microwave oscillator, said waveguide and said microwave detector, said enclosure having an opening at which said waveguide is mounted.

* * * * *